(12) United States Patent
Johnson et al.

(10) Patent No.: US 9,200,331 B2
(45) Date of Patent: Dec. 1, 2015

(54) METHODS FOR THE DIAGNOSIS OF BACTERIAL VAGINOSIS

(75) Inventors: Erik P. Johnson, Oceanside, CA (US); Dale A. Schwab, Carlsbad, CA (US)

(73) Assignee: QUEST DIAGNOSTICS INVESTMENTS INCORPORATED, Wilmington, DE (US)

( * ) Notice: Subject to any disclaimer, the term of this patent is extended or adjusted under 35 U.S.C. 154(b) by 0 days.

(21) Appl. No.: 13/511,827

(22) PCT Filed: Nov. 17, 2010

(86) PCT No.: PCT/US2010/056983
§ 371 (c)(1),
(2), (4) Date: May 24, 2012

(87) PCT Pub. No.: WO2011/068679
PCT Pub. Date: Jun. 9, 2011

(65) Prior Publication Data
US 2012/0264126 A1    Oct. 18, 2012

Related U.S. Application Data

(60) Provisional application No. 61/266,338, filed on Dec. 3, 2009.

(51) Int. Cl.
*C12Q 1/68* (2006.01)

(52) U.S. Cl.
CPC ............... *C12Q 1/689* (2013.01); *C12Q 1/686* (2013.01); *C12Q 2600/158* (2013.01)

(58) Field of Classification Search
None
See application file for complete search history.

(56) References Cited

U.S. PATENT DOCUMENTS

| 7,627,437 B2 | 12/2009 | Forney et al. |
| 2010/0075306 A1 | 3/2010 | Bretelle et al. |

FOREIGN PATENT DOCUMENTS

| WO | WO-02/10444 | 2/2002 |
| WO | WO 02/10444 A1 | 2/2002 |
| WO | WO 2008/062136 A9 | 5/2008 |

OTHER PUBLICATIONS

Harmsen et al., Microbial Ecology in Health and Disease, 1999, vol. 11, pp. 3-12.*
Vitali et al., Applied and Environmental Microbiology, 2007, pp. 5731-5741.*
Jannes et al., Diagnostic Bacterial Protocols, Methods in Molecular Biology, vol. 345, 2006, pp. 1-21.*
Menard et al., Clinical Infectious Disease, 2008, vol. 47, pp. 33-43.*
Money, Can J Infect Dis Med Microbiol, 2005, vol. 16, pp. 77-79.*
*Megasphaera hominis* sequence L79909.1, 2004, downloaded Jun. 7, 2013 from: http://www.ncbi.nlm.nih.gov/nuccore/L79909.*
*Atopobium vaginae* sequence AF325325.1, 2003, downloaded Jun. 7, 2013 from: http://www.ncbi.nlm.nih.gov/nuccore/af325325.1.*
*Lactobacillus vaginalis* sequence S000389919, 2002, downloaded Jun. 7, 2013 from: http://rdp.cme.msu.edu/segmatch/segmatch_seqrecorddetail.jsp?segid=S000389919.*
*Lactobacillus crispatus* sequence S000003123, 1999, downloaded Jun. 7, 2013 from: http://rdp.cme.msu.edu/segmatch/segmatch_seqrecorddetail.jsp?segid=S000003123.*
*Lactobacillus jensenii* sequence S000389885, 2002, downloaded Jun. 7, 2013 from: http://rdp.cme.msu.edu/seqmatch/seqmatch_seqrecorddetail.jsp?seqid=S000389885.*
*Gardnerella vaginalis* sequence S000436355, downloaded Jun. 7, 2013 from: http://rdp.cme.msu.edu/seqmatch/seqmatch_seqrecorddetail.jsp?seqid=S000436355.*
International Search Report and Written Opinion mailed May 2, 2011, in corresponding PCT/US2010/056983.
DeBacker et al., "Quantitative determination by real-time PCR of four vaginal *Lactobacillus* species, *Gardnerella vaginalis* and *Atopobium vaginae* indicates an inverse relationship between L. gasseri and L. lners," BMC Microbiology, 2007, 7:115, 1-13.
Menard et al., "Molecular Quanitification of *Gardnerella vaginalis* and *Atopobium vaginae* Loads to Predict Bacterial Vaginosis," Clinical Infectious Diseases, 2008, 47:33-43.
Witt et al., "DNA Hybridization Test: Rapid Diagnostic Tool for Excluding Bacterial Vaginosis in Pregnant Women with Symptoms Suggestive of Infection," Journal of Clinical Microbiology, Aug. 2002, 3057-3059.
Zariffard et al., "Detection of bacterial vaginosis-related organisms by real-time PCR for *Lactobacilli*, *Gardnerella vaginalis* and *Mycoplasma hominis*," FEMS Immunology and Medical Microbiology, 2002, 34:277-281.
First Office Action in Chinese Application No. 201080063023.7 dtd Jul. 16, 2013 (English translation, 7 pages).
Sequence AF375895.1, The European Bioinformatics Institute, accessed at http://www.ebi.ac.uk/ena/data/view/AF375895 on Nov. 8, 2013. (3 pages).
Zhang, B., "Pathogens of Bacterial Vaginosis, Patients, Detection, and Analysis," Chinese Journal of Clinical Rational Drug Use, vol. 2, No. 22, p. 67, 2009. (Chinese language document only).
EP Application No. 10834939 Search Report dated May 17, 2013.
Tamrakar, et al., "Association between *Lactobacillus* species and bacterial vaginosis-related bacteria, and barterial vaginosis scores in pregnant Japanese women", BMC Infectious Diseases, vol. 7, No. 1, p. 1-8, (2007).
1 Fredricks et al., "Changes in Vaginal Bacterial Concentrations with Intravaginal Metronidazole Therapy for Bacterial Vaginosis as Assessed by Quantitative PCR," Journal of Clinical Microbiology, ' vol. 47, No. 3, pp. 721-726, Mar. 2009.

* cited by examiner

*Primary Examiner* — Michele K Joike
*Assistant Examiner* — Mindy G Brown
(74) *Attorney, Agent, or Firm* — Foley & Lardner LLP

(57) ABSTRACT

The present invention relates to methods for the diagnosis of bacterial vaginosis based on an analysis of a patient sample. For example, patient test samples are analyzed for the presence or absence of one or more *lactobacilli* and two or more pathogenic organisms. The presence or absence of one or more *lactobacilli* and two or more pathogenic organisms may be detected using PCR analysis of nucleic acid segments corresponding to each target organism. The quantity of the target organisms can then be used to determine a score which is indicative of a diagnosis of bacterial vaginosis.

2 Claims, 2 Drawing Sheets

SEQUENCE LISTING

<160> NUMBER OF SEQ ID NOS: 22

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tgccccatag tctgggatac                                                 20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
atgtggccga tcagtctctc                                                 20

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
ccggataaga aagcagatcg catga                                           25

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
agtaacgcgt gggtaacctg                                                 20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gtccatcctt tagcgacagc                                                 20

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 6
ccggataaaa gctactttcg catga                                           25

```
<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 7
ccggataaga aagcagatcg catga                                              25

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
acacggccca aactcctac                                                     19

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cgatccgaaa accttcttca                                                    20

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 10
ccgaatgatg caatcaactt cgag                                               24

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11 tagggagcg aacaggatta                                                     20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
cccgtcaatt cctttgagtt                                                    20
```

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 13
tggggagatt atactttccg tgccg                                              25

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cacattggga ctgagacacg                                                    20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
acgcttgcca cctacgtatt                                                    20

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 16
acggtaccgt aagagaaagc cacgg                                              25

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ctcttggaaa cgggtggtaa                                                    20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gagtctgggc cgtatctcag                                                    20

```
<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 19
agcttgtagg cggggtaatg gcc                                          23

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gagtaacacg tgggcaacct                                              20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gcccatcctg aagtgatagc                                              20

<210> SEQ ID NO 22
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 22
ctgaagcggg ggataacatc tggaa                                        25
```

METHODS FOR THE DIAGNOSIS OF BACTERIAL VAGINOSIS

CROSS-REFERENCE TO RELATED APPLICATIONS

This application is a National Stage application of PCT/US2010/056983, filed Nov. 17, 2010, which claims priority from U.S. Provisional Application No. 61/266,338, filed Dec. 3, 2009.

The instant application contains a Sequence Listing which has been submitted in ASCII format via EFS-WEB and is hereby incorporated by reference in its entirety. Said ASCII copy, created on May 21, 2012, is named sequence.txt and is 6 KB.

FIELD OF THE INVENTION

The present technology relates generally to the field of medical diagnostics. In particular, the present technology relates to methods of detecting the presence or absence of bacteria associated with bacterial vaginosis, and determining a diagnostic score based on the presence or absence of the bacteria.

BACKGROUND OF THE INVENTION

The following description is provided to assist the understanding of the reader. None of the information provided or references cited is admitted to be prior art to the present invention.

Vaginitis is the most common gynecological problem in adult women. Infectious vaginitis presents itself in three primary forms: bacterial vaginosis, candidal vaginitis, and trichomonas vaginitis. Bacterial vaginosis, which affects up to 25% of American women in normal clinical populations, is nearly twice as common as candida and is the most common form of vaginal infection. Bacterial vaginosis is caused by a replacement of the normal vaginal flora with facultative anaerobic bacteria. Typically, the symptoms of bacterial vaginosis are non-specific and differential diagnosis is problematic.

Complications associated with bacterial vaginosis represent a major health care cost burden. For example, obstetric complications of bacterial vaginosis include preterm labor/birth, low birth weight babies; premature rupture of the amniotic membranes; amniotic fluid infections; postpartum endometritis; and chorioamnionitis. Also, bacterial vaginosis is suspected of being one of the many causes of cerebral palsy. In addition, gynecologic complications of bacterial vaginosis include postoperative infections; pelvic inflammatory disease (PID); abnormal cervical cytology, increased susceptibility to sexually transmitted diseases (STDs), and post-hysterectomy infections. Furthermore, bacterial vaginosis may potentially be a cofactor with human papilloma virus in the development of cervical intraepithelial neoplasia (CIN), a precursor of cervical cancer.

Diagnosis of BV has traditionally been performed using the Amsel's criteria, which include any three of: abnormal vaginal discharge, pH of more than 4.5, foul odor after the addition of potassium hydroxide, or presence of clue cells in Gram stain; or by the calculation of a Nugent score. The Nugent score is determined from a microscopic test measuring the relative number of *Lactobacillus* ssp., *Gardnerella vaginalis*, *Bacteroides* ssp., and *Mobiluncus*-like species.

SUMMARY OF THE INVENTION

In one aspect, the present invention provides a method for diagnosing bacterial vaginosis in a subject, the method comprising: (a) determining a single diagnostic score using the levels of one or more *lactobacilli* and two or more pathogenic organisms in a sample from the subject; and (b) comparing the diagnostic score for the individual to a reference score to determine the presence of bacterial vaginosis, wherein said single diagnostic score is determined by finding the ratio of a logarithmic function of the levels of the one or more *lactobacilli* and a logarithmic function of the levels of the two or more pathogenic organisms. In one embodiment, the sample is a vaginal swab.

In one embodiment, the logarithmic function applied to the one or more *lactobacilli* comprises determining the sum of the logarithm of the level of each *lactobacilli* used, and the logarithmic function applied to the two or more pathogenic organisms comprises determining the sum of the logarithm of the level of each pathogenic organism used. In one embodiment, the reference score is about 0.2, and a diagnostic score less than about 0.2 is indicative of the presence of bacterial vaginosis.

In one embodiment, the logarithmic function applied to the one or more *lactobacilli* comprises determining the logarithm of the sum the levels of each *lactobacilli* used, and the logarithmic function applied to the two or more pathogenic organisms comprises determining the logarithm of the sum of the levels of each pathogenic organism used. In one embodiment, the reference score is about 0.2, and a diagnostic score less than about 0.2 is indicative of the presence of bacterial vaginosis.

In one embodiment, the levels of one or more *lactobacilli* and two or more pathogenic organisms in the sample are determined by detecting nucleic acids indicative of the one or more *lactobacilli* and two or more pathogenic organisms. In one embodiment, the detecting is by PCR, RT-PCR, or nucleic acid hybridization. In one embodiment, the detecting comprises amplifying a fragment from each of the one or more *lactobacilli* and two or more pathogenic organisms in the sample, if present. In one embodiment, the fragment is a fragment of a 16S ribosomal RNA gene. In an illustrative embodiment, the detecting is accomplished using the TaqMan® PCR detection system.

In one embodiment, the one or more *lactobacilli* are selected from the group consisting of *Lactobacillus acidophilus*, *Lactobacillus crispatus*, *Lactobacillus jensenii*, *Lactobacillus iners* and *Lactobacillus vaginalis*. In one embodiment, the levels of one or more *lactobacilli* are detected using primers capable of detecting *Lactobacillus* spp. In one embodiment, at least one of the primers capable of detecting *Lactobacillus* spp. are selected from the group consisting of SEQ ID NOs: 8-9 or complements thereof.

In one embodiment, the levels of one or more *lactobacilli* are detected using one or more primer pairs capable of detecting *Lactobacillus acidophilus*, *Lactobacillus crispatus*, and *Lactobacillus jensenii*. In one embodiment, at least one of the primers capable of detecting *Lactobacillus acidophilus* and *Lactobacillus crispatus* are selected from the group consisting of SEQ ID NOs: 1-2 or complements thereof. In one embodiment, at least one of the primers capable of detecting *Lactobacillus jensenii* are selected from the group consisting of SEQ ID NOs: 4-5 or complements thereof. In one embodiment, at least one of the primers capable of detecting *Lactobacillus vaginalis* are selected from the group consisting of SEQ ID NO: 20-21 or complements thereof.

In one embodiment, at least one of the two or more pathogenic organisms is selected from the group consisting of *Atopobium vaginae*, *Megasphaera* ssp., and *Gardnerella vaginalis*. In one embodiment, at least one of the primers capable of detecting *Atopobium vaginae* are selected from the group consisting of SEQ ID NOs: 11-12 or complements thereof. In one embodiment, at least one of the primers capable of detecting *Megasphaera* ssp. are selected from the group consisting of SEQ ID NOs: 14-15 or complements thereof. In one embodiment, at least one of the primers capable of detecting *Gardnerella vaginalis* are selected from the group consisting of SEQ ID NOs: 17-18 or complements thereof.

In specific embodiments of any of the foregoing the logarithmic function may be any one of Algorithms 1-10 identified herein. The specific organisms identified in the algorithms are intended merely as examples. The measured level of any of the *lactobacilli* species may be substituted for the measured level of any other non-pathogenic *lactobacillus*. And, the measured level of any of the pathogenic bacteria may be substituted with the level of any other pathogenic bacteria.

In one aspect, the present invention provides a kit for diagnosing bacterial vaginosis comprising a primer pair for amplifying a fragment of a nucleic acid from one or more *lactobacilli* and primer pairs for amplifying fragments of nucleic acids from two or more pathogenic organisms. In one embodiment, at least one primer pair is selected from the group consisting of: SEQ ID NOs: 1/2, SEQ ID NOs: 4/5, SEQ ID NOs: 8/9; SEQ ID NOs: 11/12; SEQ ID NOs: 14-15; and SEQ ID NOs: 17/18 or complements thereof.

In one aspect, the present invention provides a substantially purified oligonucleotide having a sequence selected from the group consisting of SEQ ID NOs: 1-19 or complements thereof.

DETAILED DESCRIPTION

Figure 1:
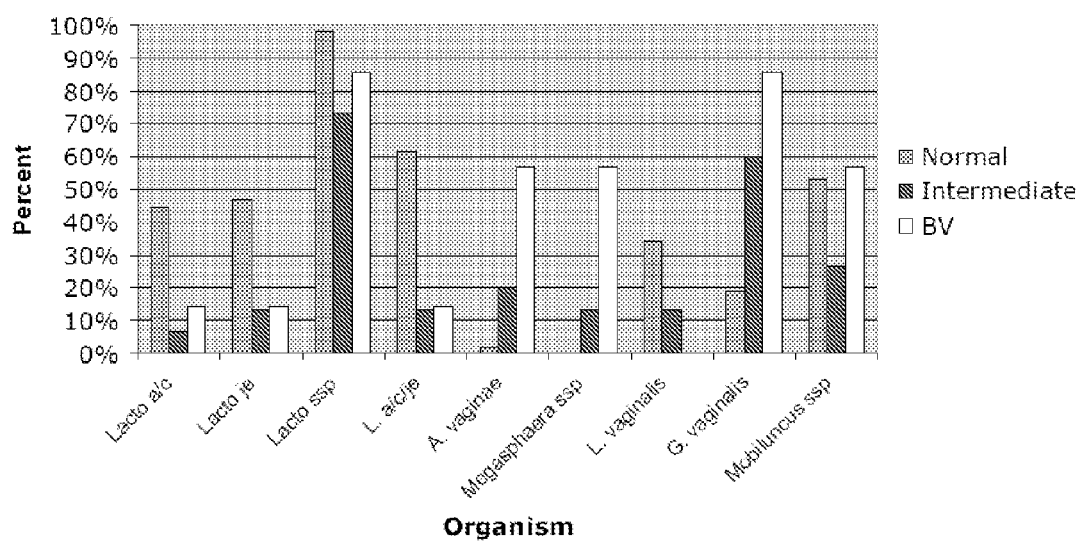
FIG. 1 is a chart showing the percent of swab specimens containing various bacterial agents arranged by Nugent Score. The bacterial agents were detected according to an illustrative embodiment of the invention.

The present invention provides methods of diagnosing bacterial vaginosis (BV) by detecting in a test nucleic acid sample from the individual one or more nucleic acid segments corresponding to various bacterial species that are relevant to a diagnosis of BV. In particular embodiments, nucleic acid segments corresponding to *lactobacilli*, and one or more pathogenic bacteria are detected. This assay can be performed in one or more subassays to detect the bacterial targets of interest. For example, one subassay detects peroxide-producing *lactobacilli* ("Assay A"); one subassay detects all *lactobacilli* ("Assay B"); one subassay detects pathogenic bacteria *Megasphaera* spp. and *Atopobium vaginae* ("Assay C"); and one subassay detects the pathogenic bacteria *Gardnerella vaginalis* ("Assay D"). This information may be used to determine whether an individual is suffering from BV. In some embodiments, a diagnostic score corresponding to a diagnosis of BV is determined. For example, the score may be determined by finding the ratio of a logarithmic function of the levels of the one or more *lactobacilli* and a logarithmic function of the levels of the two or more pathogenic organisms.

In practicing the methods described herein, many conventional techniques in molecular biology, protein biochemistry, cell biology, immunology, microbiology and recombinant DNA are used. These techniques are well-known and are explained in, e.g., *Current Protocols in Molecular Biology*, Vols. I-III, Ausubel, Ed. (1997); Sambrook et al., *Molecular Cloning: A Laboratory Manual*, Second Ed. (Cold Spring Harbor Laboratory Press, Cold Spring Harbor, N.Y., 1989); *DNA Cloning: A Practical Approach*, Vols. I and II, Glover, Ed. (1985); *Oligonucleotide Synthesis*, Gait, Ed. (1984); *Nucleic Acid Hybridization*, Hames & Higgins, Eds. (1985); *Transcription and Translation*, Hames & Higgins, Eds. (1984); *Animal Cell Culture*, Freshney, Ed. (1986); *Immobilized Cells and Enzymes* (IRL Press, 1986); Perbal, *A Practical Guide to Molecular Cloning*; the series, *Meth. Enzymol.*, (Academic Press, Inc., 1984); *Gene Transfer Vectors for Mammalian Cells*, Miller & Calos, Eds. (Cold Spring Harbor Laboratory, NY, 1987); and *Meth. Enzymol.*, Vols. 154 and 155, Wu & Grossman, and Wu, Eds., respectively.

The definitions of certain terms as used in this specification are provided below. Unless defined otherwise, all technical and scientific terms used herein generally have the same meaning as commonly understood by one of ordinary skill in the art to which this invention belongs.

As used in this specification and the appended claims, the singular forms "a", "an" and "the" include plural referents unless the content clearly dictates otherwise. For example, reference to "a nucleic acid" includes a combination of two or more nucleic acids, and the like.

The term "amplification" or "amplify" as used herein means one or more methods known in the art for copying a target nucleic acid, thereby increasing the number of copies of a selected nucleic acid sequence. Amplification may be exponential or linear. A target nucleic acid may be either DNA or RNA. The sequences amplified in this manner form an "amplicon." While the exemplary methods described hereinafter relate to amplification using the polymerase chain reaction ("PCR"), numerous other methods are known in the art for amplification of nucleic acids (e.g., isothermal methods, rolling circle methods, etc.). The skilled artisan will understand that these other methods may be used either in place of, or together with, PCR methods. See, e.g., Saiki, "Amplification of Genomic DNA" in *PCR Protocols*, Innis et al., Eds., Academic Press, San Diego, Calif. 1990, pp. 13-20; Wharam et al., *Nucleic Acids Res.*, 2001, 29(11):E54-E54; Hafner et al., *Biotechniques* 2001, 30(4):852-6, 858, 860; Zhong et al., *Biotechniques*, 2001, 30(4):852-6, 858, 860.

The term "complement" as used herein means the complementary sequence to a nucleic acid according to standard Watson/Crick base pairing rules. A complement sequence can also be a sequence of RNA complementary to the DNA sequence or its complement sequence, and can also be a cDNA. The term "substantially complementary" as used herein means that two sequences hybridize under stringent hybridization conditions. The skilled artisan will understand that substantially complementary sequences need not hybridize along their entire length. In particular, substantially complementary sequences comprise a contiguous sequence of bases that do not hybridize to a target or marker sequence, positioned 3' or 5' to a contiguous sequence of bases that hybridize under stringent hybridization conditions to a target or marker sequence.

As used herein the terms "diagnose" or "diagnosis" or "diagnosing" refer to distinguishing or identifying a disease, syndrome or condition or distinguishing or identifying a person having a particular disease, syndrome or condition. In illustrative embodiments of the invention, assays and algorithms are used to diagnose bacterial vaginosis in a subject based on an analysis of a sample.

As used herein, the term "hybridize" or "specifically hybridize" refers to a process where two complementary nucleic acid strands anneal to each other under appropriately stringent conditions. Hybridizations are typically conducted with probe-length nucleic acid molecules. Nucleic acid hybridization techniques are well known in the art. See, e.g., Sambrook, et al., 1989, *Molecular Cloning: A Laboratory Manual*, Second Edition, Cold Spring Harbor Press, Plainview, N.Y. Those skilled in the art understand how to estimate and adjust the stringency of hybridization conditions such that sequences having at least a desired level of complementarity will stably hybridize, while those having lower complementarity will not. For examples of hybridization conditions and parameters, see, e.g., Sambrook, et al., 1989, *Molecular Cloning: A Laboratory Manual*, Second Edition, Cold Spring Harbor Press, Plainview, N.Y.; Ausubel, F. M. et al. 1994, *Current Protocols in Molecular Biology*. John Wiley & Sons, Secaucus, N.J.

By "isolated", when referring to a nucleic acid (e.g., an oligonucleotide such as RNA, DNA, or a mixed polymer) is meant a nucleic acid that is apart from a substantial portion of the genome in which it naturally occurs and/or is substantially separated from other cellular components which naturally accompany such nucleic acid. For example, any nucleic acid that has been produced synthetically (e.g., by serial base condensation) is considered to be isolated. Likewise, nucleic acids that are recombinantly expressed, cloned, produced by a primer extension reaction (e.g., PCR), or otherwise excised from a genome are also considered to be isolated.

As used herein, a "fragment" means a polynucleotide that is at least about 15, 20, 25, 30, 35, 40, 45, 50, 75, 100, 200, 300, 400, 500, 1000 nucleotides or more in length.

As used herein, "nucleic acid" refers broadly to segments of a chromosome, segments or portions of DNA, cDNA, and/or RNA. Nucleic acid may be derived or obtained from an originally isolated nucleic acid sample from any source (e.g., isolated from, purified from, amplified from, cloned from, or reverse transcribed from sample DNA or RNA).

As used herein, the term "oligonucleotide" refers to a short polymer composed of deoxyribonucleotides, ribonucleotides or any combination thereof. Oligonucleotides are generally between about 10 and about 100 nucleotides in length. Oligonucleotides are preferably 15 to 70 nucleotides long, with 20 to 26 nucleotides being the most common. An oligonucleotide may be used as a primer or as a probe.

An oligonucleotide is "specific" for a nucleic acid if the oligonucleotide has at least 50% sequence identity with a portion of the nucleic acid when the oligonucleotide and the nucleic acid are aligned. An oligonucleotide that is specific for a nucleic acid is one that, under the appropriate hybridization or washing conditions, is capable of hybridizing to the target of interest and not substantially hybridizing to nucleic acids which are not of interest. Higher levels of sequence identity are preferred and include at least 75%, at least 80%, at least 85%, at least 90%, or at least 95% sequence identity.

As used herein, a "primer" for amplification is an oligonucleotide that specifically anneals to a target or marker nucleotide sequence. The 3' nucleotide of the primer should be identical to the target or marker sequence at a corresponding nucleotide position for optimal primer extension by a polymerase. As used herein, a "forward primer" is a primer that anneals to the anti-sense strand of double stranded DNA (dsDNA). A "reverse primer" anneals to the sense-strand of dsDNA.

As used herein, the term "sample" or "test sample" refers to any liquid or solid material containing nucleic acids. In suitable embodiments, a test sample is obtained from a biological source (i.e., a "biological sample"), such as cells in culture or a tissue sample from an animal, most preferably, a human. In an exemplary embodiment, the sample is a vaginal swab.

"Target nucleic acid" as used herein refers to segments of a chromosome, a complete gene with or without intergenic sequence, segments or portions a gene with our without intergenic sequence, or sequence of nucleic acids to which probes or primers are designed. Target nucleic acids may include wild type sequences, nucleic acid sequences containing mutations, deletions or duplications, tandem repeat regions, a gene of interest, a region of a gene of interest or any upstream or downstream region thereof. Target nucleic acids may represent alternative sequences or alleles of a particular gene. Target nucleic acids may be derived from genomic DNA, cDNA, or RNA. As used herein target nucleic acid may be native DNA or a PCR amplified product. In one embodiment, the target nucleic acid is a fragment of a 16S ribosomal RNA gene from a bacterial species.

As used herein the term "stringency" is used in reference to the conditions of temperature, ionic strength, and the presence of other compounds, under which nucleic acid hybridizations are conducted. With high stringency conditions, nucleic acid base pairing will occur only between nucleic acids that have sufficiently long segments with a high frequency of complementary base sequences. Exemplary hybridization conditions are as follows. High stringency generally refers to conditions that permit hybridization of only those nucleic acid sequences that form stable hybrids in 0.018M NaCl at 65° C. High stringency conditions can be provided, for example, by hybridization in 50% formamide, 5×Denhardt's solution, 5×SSC (saline sodium citrate) 0.2% SDS (sodium dodecyl sulphate) at 42° C., followed by washing in 0.1×SSC, and 0.1% SDS at 65° C. Moderate stringency refers to conditions equivalent to hybridization in 50% formamide, 5×Denhardt's solution, 5×SSC, 0.2% SDS at 42° C., followed by washing in 0.2×SSC, 0.2% SDS, at 65° C. Low stringency refers to conditions equivalent to hybridization in 10% formamide, 5×Denhardt's solution, 6×SSC, 0.2% SDS, followed by washing in 1×SSC, 0.2% SDS, at 50° C.

As used herein, the term "patient" refers to a subject who receives medical care, attention or treatment. As used herein, the term is meant to encompass a person having or suspected of having a disease including a person who may be symptomatic for a disease but who has not yet been diagnosed.

As used herein, the term "pathogens", and grammatical equivalents, refers to microorganisms which are associated with disease states, e.g., bacterial vaginosis. A pathogen may include organisms that are considered commensals but under certain conditions can participate in a pathogenic process. Thus, pathogenic organisms that participate in formation of bacterial vaginosis include *Gardnerella vaginalis* which under other circumstances may be classified as a commensal. Pathogens may be characterized by their extracellular components, e.g., proteins, etc., which are secreted, produced, or otherwise discharged by the pathogen, thereby causing the subject to be afflicted with a disease state associated with the pathogen. As disclosed herein, pathogens associated with bacterial vaginosis include, but are not limited to, *Gardnerella vaginalis, Atopobium vaginae*, and *Megasphaera* spp. The term "pathogen" is also intended to encompass presently unknown infectious agents that may be discovered in the future, since their characterization as a pathogen will be readily determinable by persons skilled in the art.

Assays for the Detection of Bacterial Vaginosis

Bacterial vaginosis (BV) is the most common vaginal infection in women, and is characterized by an imbalance of the normal vaginal flora. In one aspect, the present invention provides methods for detecting the presence or absence of bacteria associated with BV, and determining a diagnostic score based on the presence or absence of the bacteria. While not wishing to be limited by theory, the presence of various *Lactobacillus* species is believed to be protective for BV, while the presence of one or more pathogens, such as *Gardnerella*, *Mobiluncus*, *Bacteroides*, *Atopobium* and *Megasphaera* species, are believed to be some of the indicators of disease. No single one of these is necessary and sufficient to give a diagnosis of BV, however, a score based on the presence or absence of these bacteria is useful in the diagnosis of BV (see next section).

In one embodiment, an assay for BV involves detecting nucleic acid segments corresponding to various bacterial species that are relevant to a diagnosis of BV. Nucleic acid segments may be detected in a variety of ways, which are described in further detail below. In one embodiment, an assay for BV may be performed using PCR. In a particular embodiment, the assay for BV may be performed using a multiplex PCR format. In one embodiment, a test is performed in two wells, both in a multiplex format. For example, one well may include tests for *lactobacilli*, while the other contains tests for *Atopobium vaginae* and the genus *Megasphaera*. In another example, one well includes tests for *lactobacilli*, while the other contains tests for the pathogens *Atopobium vaginae*, the genus *Megasphaera*, and *Gardnerella vaginalis*.

In one aspect, the methods described herein are designed to detect various *lactobacilli* and pathogenic species associated with BV. Assays may be combined in various configurations in a multiplex format. One subassay, referred to herein as the "Assay A", includes one test for the detection for the closely related species *Lactobacillus acidophilus* and *Lactobacillus crispatus*, and another for the detection of *Lactobacillus jensenii*. All three of these species are peroxide producers and negatively correlate to disease. Exemplary TaqMan® primers and probes for the Peroxides assay are shown in Table 1.

TABLE 1

Exemplary Primers and Probes for Assay A

| Reagent Name | Bacterial Target(s) | Sequence (5' to 3') | SEQ ID NO: |
|---|---|---|---|
| Lacto a/c Forward | L. acidophilus L. crispatus | 5'-TGCCCCATAGTCTGGGATAC-3' | 1 |
| Lacto a/c Reverse | L. acidophilus L. crispatus | 5'-ATGTGGCCGATCAGTCTCTC-3' | 2 |
| Lacto a/c Probe | L. acidophilus L. crispatus | 5'-[Q670]-CCGGATAAGAAAGCAGATCGCATGA-[BHQ2]-3' | 3 |
| Lacto je Forward | L. jensenii | 5'-AGTAACGCGTGGGTAACCTG-3' | 4 |
| Lacto je Reverse | L. jensenii | 5'-GTCCATCCTTTAGCGACAGC-3' | 5 |
| Lacto je Probe | L. jensenii | 5'-[FAM]-CCGGATAAAAGCTACTTTCGCATGA-[BHQ1]-3' | 6 |

A second subassay, referred to herein as the "Assay B", includes the same tests for *L. acidophilus/crispatus* and *L. jensenii* as the Assay A, but also includes a third test, the *Lactobacillus* ssp. assay, which detects all members of the *Lactobacillus* genus. Optionally, Assay B may further include an assay to detect *L. vaginalis*. While all *lactobacilli* have not been shown to correlate to BV disease state, Assay B may provide useful information in the event that none of the peroxide producing species from Assay A are present in a clinical sample. Exemplary primers and probes for Assay B are shown in Table 2.

TABLE 2

Exemplary Primers and Probes for Assay B

| Reagent Name | Bacterial Target(s) | Sequence (5' to 3') | SEQ ID NO: |
|---|---|---|---|
| Lacto a/c Forward | L. acidophilus L. crispatus | 5'-TGCCCCATAGTCTGGGATAC-3' | 1 |
| Lacto a/c Reverse | L. acidophilus L. crispatus | 5'-ATGTGGCCGATCAGTCTCTC-3' | 2 |
| Lacto a/c Probe | L. acidophilus L. crispatus | 5'-[FAM]-CCGGATAAGAAAGCAGATCGCATGA-[BHQ1]-3' | 7 |
| Lacto je Forward | L. jensenii | 5'-AGTAACGCGTGGGTAACCTG-3' | 4 |

TABLE 2-continued

Exemplary Primers and Probes for Assay B

| Reagent Name | Bacterial Target(s) | Sequence (5' to 3') | SEQ ID NO: |
|---|---|---|---|
| Lacto je Reverse | L. jensenii | 5'-GTCCATCCTTTAGCGACAGC-3' | 5 |
| Lacto je Probe | L. jensenii | 5'-[FAM]-CCGGATAAAAGCTACTTTCGCATGA-[BHQ1]-3' | 6 |
| Lacto ssp Forward | Lactobacillus spp. | 5'-ACACGGCCCAAACTCCTAC-3' | 8 |
| Lacto ssp Reverse | Lactobacillus spp. | 5'-CGATCCGAAAACCTTCTTCA-3' | 9 |
| Lacto ssp Probe | Lactobacillus spp. | 5'-[Q670]-CCGAATGATGCAATCAACTTCGAG-[BHQ2]-3' | 10 |
| Lv Forward | L. vaginalis | 5-GAGTAACACGTGGGCAACCT-3' | 20 |
| Lv Reverse | L. vaginalis | 5'-GCCCATCCTGAAGTGATAGC-3' | 21 |
| Lv Probe | L. vaginalis | 5'-[FAM]-CTGAAGCGGGGATAACATCTGGAA-3' | 22 |

A third subassay, referred to herein as the "Assay C," will detect *Atopobium vaginae* and the genus *Megasphaera*. While not wishing to be limited by theory, these pathogens may correlate more highly to BV disease than *Gardnerella vaginalis* and *Mobiluncus* sp., two agents used to determine disease state using the Nugent score. In some embodiments, *Gardnerella* may be detected separately as "Assay D". Exemplary primers and probes for the detection of pathogenic agents are shown in Table 3.

TABLE 3

Exemplary Primers and Probes for Assays C and D

| Reagent Name | Bacterial Target(s) | Sequence (5' to 3') | SEQ ID NO: |
|---|---|---|---|
| Av Forward | Atopobium vaginae | 5'-TAGGGGAGCGAACAGGATTA-3' | 11 |
| Av Reverse | Atopobium vaginae | 5'-CCCGTCAATTCCTTTGAGTT-3' | 12 |
| Av Probe | Atopobium vaginae | 5'-[FAM]-TGGGGAGATTATACTTTCCGTGCCG-[BHQ1]-3' | 13 |
| Mega Forward | Megasphaera spp. | 5'-CACATTGGGACTGAGACACG-3' | 14 |
| Mega Reverse | Megasphaera spp. | 5'-ACGCTTGCCACCTACGTATT-3' | 15 |
| Mega Probe | Megasphaera spp. | 5'-[Q670]-ACGGTACCGTAAGAGAAAGCCACGG-[BHQ1]-3' | 16 |
| Gv Forward | Gardnerella spp. | 5'-CTCTTGGAAACGGGTGGTAA-3' | 17 |
| Gv Reverse | Gardnerella spp. | 5'-GAGTCTGGGCCGTATCTCAG-3' | 18 |
| Gv Probe | Gardnerella spp. | 5'-[Q670]-AGCTTGTAGGCGGGGTAATGGCC-[BHQ1]-3' | 19 |

With regard to the exemplary primers and probes, those skilled in the art will readily recognize that nucleic acid molecules may be double-stranded molecules and that reference to a particular site on one strand refers, as well, to the corresponding site on a complementary strand. In defining a variant position, allele, or nucleotide sequence, reference to an adenine, a thymine (uridine), a cytosine, or a guanine at a particular site on one strand of a nucleic acid molecule also defines the thymine (uridine), adenine, guanine, or cytosine (respectively) at the corresponding site on a complementary strand of the nucleic acid molecule. Thus, reference may be made to either strand in order to refer to a particular variant position, allele, or nucleotide sequence. Probes and primers, may be designed to hybridize to either strand and detection methods disclosed herein may generally target either strand.

Determination of a Diagnostic Score

In one aspect, the present invention provides methods for diagnosing bacterial vaginosis in a subject by mathematically determining a single diagnostic score using the levels of one or more *lactobacilli* and two or more pathogenic organisms in a sample from the subject; and comparing the diagnostic score for the individual to one or more reference scores to determine the presence of bacterial vaginosis. In some embodiments, the single diagnostic score is determined by finding the ratio of a logarithmic function of the levels of one or more *lactobacilli* and a logarithmic function of the levels of two or more pathogenic organisms.

Thus, in embodiments of this aspect, an algorithm may be used to determine a single diagnostic score. In one embodiment, an algorithm is used to determine a single diagnostic score based on cell counts measured in a real-time PCR assay, e.g., TaqMan®, for one or more *lactobacilli* and two or more pathogenic organisms. Results for *lactobacilli* are then subjected to a logarithmic function and divided by results for pathogenic organisms subjected to a logarithmic function to produce a ratio. Illustrative algorithms are presented as Algorithms 1-8 below.

In some embodiments, the logarithmic functions include summing the logarithms of the quantities of each target organism (i.e., the Sum of Logs method). Algorithm 1, shown below, demonstrates a generic form of the Sum of Logs method. Illustrative Algorithms 2-5, also shown below, demonstrate exemplary embodiments of the Sum of Logs method.

In other embodiments, the logarithmic functions include taking the logarithm of the sum of the quantities of each target organism (i.e., the Log of Sums method). Algorithm 6, shown below, demonstrates a generic form of the Log of Sums method. Illustrative Algorithms 7-10, shown below, demonstrate exemplary embodiments of the Logs of Sums method.

While not wishing to be limited by theory, using the Sum of Logs method emphasizes the total contribution of all organisms in the calculation, while the Log of Sums method emphasizes the most common organism.

$$\frac{\sum \text{Log}(\text{one or more natural flora including a } lactobacilli)}{\sum \text{Log}(\text{two or more pathogenic organisms})} \quad \text{Algorithm 1}$$

$$\frac{\text{Log}(Lactobacillus\ spp.) + \text{Log}(Assay\ A)}{\text{Log}(Atopobium\ vaginae) + \text{Log}(Megaphaera\ ssp.)} \quad \text{Algorithm 2}$$

$$\frac{\text{Log}(L.acidophilus/crispatus) + \text{Log}(L\ jensenii)}{\text{Log}(Atopobium\ vaginae) + \text{Log}(Megaphaera\ ssp.)} \quad \text{Algorithm 3}$$

$$\frac{\text{Log}(L.acidophilus/crispatus) + \text{Log}(L\ jensenii)}{\text{Log}(Atopobium\ vaginae) + \text{Log}(Megaphaera\ ssp.) + \text{Log}(Gardnerella)} \quad \text{Algorithm 4}$$

$$\frac{\text{Log}(L.acidophilus/crispatus) + \text{Log}(L\ jensenii) + \text{Log}(L.Vaginalis)}{\text{Log}(Atopobium\ vaginae) + \text{Log}(Megaphaera\ ssp.) + \text{Log}(Gardnerella)} \quad \text{Algorithm 5}$$

$$\frac{\text{Log}(\sum \text{ (one or more natural flora including a } lactobacilli))}{\text{Log}(\sum \text{ (two or more pathogenic organisms)})} \quad \text{Algorithm 6}$$

$$\frac{\text{Log}(Lactobacillus\ spp.+Assay\ A)}{\text{Log}(Atopobium\ vaginae + Megaphaera\ ssp.)} \quad \text{Algorithm 7}$$

$$\frac{\text{Log}(L.acidophilus/crispatus + L\ jensenii)}{\text{Log}(Atopobium\ vaginae + Megaphaera\ ssp.)} \quad \text{Algorithm 8}$$

$$\frac{\text{Log}(L.acidophilus/crispatus + L\ jensenii)}{\text{Log}(Atopobium\ vaginae + Megaphaera\ ssp.+Gardnerella)} \quad \text{Algorithm 9}$$

$$\frac{\text{Log}(L.acidophilus/crispatus + L\ jensenii + L.vaginalis)}{\text{Log}(Atopobium\ vaginae + Megaphaera\ ssp.+Gardnerella)} \quad \text{Algorithm 10}$$

In an exemplary embodiment, ratio values above an upper reference score of about 5, such as about 4.5, 4.75, 5, 5.25, and 5.5, are given a diagnosis of "Normal", values between a lower reference score and the upper reference score are given a diagnosis of "Intermediate". The lower reference score is typically about 0.2, such as 0.15, 0.18, 0.2, 0.22, and 0.25. Values below the lower reference score are given a diagnosis as positive for bacterial vaginosis ("BV").

A device may be configured to calculate a single diagnostic score and predict the presence of bacterial vaginosis in an individual. The device may comprise an input interface configured to receive data, which input interface is in data communication with a processor, which is in data communication with an output interface. In various embodiments the device could be a handheld device, computer, a laptop, portable device, a server, or the like.

The input interface is used for entry of data including levels of *lactobacilli* and pathogenic organisms as determined from a sample from the individual. Data may be entered manually by an operator of the system using an input interface such as a keyboard or keypad. Alternatively, data may be entered electronically, when the input interface is a cable in data communication with a computer, a network, a server, or analytical instrument. The input interface may wirelessly communicate with the processor.

The device further comprises a processor and a computer-readable storage medium including computer-readable instructions stored therein that, upon execution by the processor, cause the device to compute a single diagnostic score. In embodiments utilizing such a device, the diagnostic score is computed using an algorithm. In some embodiments, the algorithm used to compute the single diagnostic score may comprise one or more of illustrative Algorithms 1-10 above. In embodiments utilizing a plurality of algorithms for determining the single diagnostic score, the results of the determination of each algorithm may be combined by any method known in the art.

In another embodiment, the device may further comprise readable instructions (e.g. software) stored on a computer-readable storage medium (e.g. memory) that, upon execution by the processor, compares the diagnostic score to one or more reference scores to predict the presence of bacterial vaginosis. A diagnostic score less than a lower reference score is predictive of bacterial vaginosis. A diagnostic score greater than an upper reference score value is predictive of the absence of bacterial vaginosis. Exemplary values for use as reference scores in these embodiments are described above. The computer-readable instructions may be executable instructions such as program code.

In one embodiment, the data output interface, in data communication with the processor, receives the diagnosis or the diagnostic score from the processor and provides the prediction or the diagnostic score to the device operator. The output interface may be, for example, a video display monitor or a printer. The output interface may be wirelessly connected to the processor. In a particular embodiment, a single device may function as the input interface and the output interface. One example of this type of interface is where the display monitor also functions as a keypad or touchscreen.

In another embodiment, a semi-quantitative algorithm is used to diagnose BV. For example, this semi-quantitative algorithm does not use a calculation, but rather considers the presence or absence of key organisms (see Table 13). A sample is considered normal (not indicative of BV) if:

(1) *L. acidophilus, L. crispatus,* or *L. jensenii* are present, *Atopobium* and *Megasphaera* are absent, and *Gardnerella* is present in amounts less than $10^6$ cells/ml; or (2) all organisms are absent.

A sample is intermediate if:

(1) the sample contains both *lactobacilli* and at least one pathogen ($\geq 10^6$ cells/ml for *Gardnerella*); or (2) all organisms are absent except for *Gardnerella*, which is present, but is less than $10^6$ cells/ml.

A sample is considered to indicate BV if no *lactobacilli* are present, and at least one pathogen is present ($\geq 10^6$ cells/ml for *Gardnerella*).

Sample Collection and Preparation

The methods and compositions of this invention may be used to detect nucleic acids associated with various bacteria using a biological sample obtained from an individual. The nucleic acid (DNA or RNA) may be isolated from the sample according to any methods well known to those of skill in the art. Biological samples may be obtained by standard procedures and may be used immediately or stored, under conditions appropriate for the type of biological sample, for later use.

Starting material for the detection assays is typically a clinical sample, which is suspected to contain a *lactobacillus* and/or a pathogenic organism. An example of a clinical sample is a vaginal swab. Next, the nucleic acids may be separated from proteins and sugars present in the original sample. Any purification methods known in the art may be used in the context of the present invention. Nucleic acid sequences in the sample can successfully be amplified using in vitro amplification, such as PCR. Typically, any compounds that may inhibit polymerases are removed from the nucleic acids.

Methods of obtaining test samples are well known to those of skill in the art and include, but are not limited to, aspirations, tissue sections, swabs, drawing of blood or other fluids, surgical or needle biopsies, and the like. The test sample may be obtained from an individual or patient. The test sample may contain cells, tissues or fluid obtained from a patient suspected being afflicted with bacterial vaginosis. The test sample may be a cell-containing liquid or a tissue. Samples may include, but are not limited to, cells from a vaginal swab, amniotic fluid, biopsies, blood, blood cells, bone marrow, fine needle biopsy samples, peritoneal fluid, amniotic fluid, plasma, pleural fluid, saliva, semen, serum, tissue or tissue homogenates, frozen or paraffin sections of tissue. Samples may also be processed, such as sectioning of tissues, fractionation, purification, or cellular organelle separation.

If necessary, the sample may be collected or concentrated by centrifugation and the like. The cells of the sample may be subjected to lysis, such as by treatments with enzymes, heat, surfactants, ultrasonication, or a combination thereof. The lysis treatment is performed in order to obtain a sufficient amount of nucleic acid derived from the bacterial cells in the same to detect using polymerase chain reaction.

Nucleic Acid Extraction and Amplification

The nucleic acid to be amplified may be from a biological sample such as a bacterial organism, cell culture, tissue sample, and the like. Various methods of extraction are suitable for isolating the DNA or RNA. Suitable methods include phenol and chloroform extraction. See Maniatis et al., *Molecular Cloning, A Laboratory Manual,* 2d, Cold Spring Harbor Laboratory Press, page 16.54 (1989). Numerous commercial kits also yield suitable DNA and RNA including, but not limited to, QIAamp™ mini blood kit, Agencourt Genfind™, Roche Cobas® Roche MagNA Pure® or phenol:chloroform extraction using Eppendorf Phase Lock Gels®, and the NucliSens extraction kit (Biomerieux, Marcy l'Etoile, France).

Nucleic acid extracted from cells or tissues can be amplified using nucleic acid amplification techniques well know in the art. By way of example, but not by way of limitation, these techniques can include the polymerase chain reaction (PCR), reverse transcriptase polymerase chain reaction (RT-PCR), nested PCR, ligase chain reaction. See Abravaya, K., et al., *Nucleic Acids Research,* 23:675-682, (1995), branched DNA signal amplification, Urdea, M. S., et al., *AIDS,* 7 (suppl 2):S11-S 14, (1993), amplifiable RNA reporters, Q-beta replication, transcription-based amplification, boomerang DNA amplification, strand displacement activation, cycling probe technology, isothermal nucleic acid sequence based amplification (NASBA). See Kievits, T. et al., *J Virological Methods,* 35:273-286, (1991), Invader® Technology, or other sequence replication assays or signal amplification assays. These methods of amplification each described briefly below and are well-known in the art.

Some methods employ reverse transcription of RNA to cDNA. As noted, the method of reverse transcription and amplification may be performed by previously published or recommended procedures. Various reverse transcriptases may be used, including, but not limited to, MMLV RT, RNase H mutants of MMLV RT such as Superscript and Superscript II (Life Technologies, GIBCO BRL, Gaithersburg, Md.), AMV RT, and thermostable reverse transcriptase from *Thermus thermophilus*. For example, one method, but not the only method, which may be used to convert RNA extracted from plasma or serum to cDNA is the protocol adapted from the Superscript II Preamplification system (Life Technologies, GIBCO BRL, Gaithersburg, Md.; catalog no. 18089-011), as described by Rashtchian, A., *PCR Methods Applic.,* 4:S83-S91, (1994).

LCR is a method of DNA amplification similar to PCR, except that it uses four primers instead of two and uses the enzyme ligase to ligate or join two segments of DNA. LCR can be performed as according to Moore et al., *J Clin Micro,* 36(4):1028-1031 (1998). Briefly, an LCR reaction mixture contains two pair of primers, dNTP, DNA ligase and DNA polymerase representing about 90 µl, to which is added 100 µl of isolated nucleic acid from the target organism. Amplification is performed in a thermal cycler (e.g., LCx of Abbott Labs, Chicago, Ill.).

TAS is a system of nucleic acid amplification in which each cycle is comprised of a cDNA synthesis step and an RNA transcription step. In the cDNA synthesis step, a sequence recognized by a DNA-dependent RNA polymerase (i.e., a polymerase-binding sequence or PBS) is inserted into the cDNA copy downstream of the target or marker sequence to be amplified using a two-domain oligonucleotide primer. In the second step, an RNA polymerase is used to synthesize multiple copies of RNA from the cDNA template. Amplification using TAS requires only a few cycles because DNA-dependent RNA transcription can result in 10-1000 copies for each copy of cDNA template. TAS can be performed according to Kwoh et al., *PNAS*, 86:1173-7 (1989). Briefly, extracted RNA is combined with TAS amplification buffer and bovine serum albumin, dNTPs, NTPs, and two oligonucleotide primers, one of which contains a PBS. The sample is heated to denature the RNA template and cooled to the primer annealing temperature. Reverse transcriptase (RT) is added the sample incubated at the appropriate temperature to allow cDNA elongation. Subsequently T7 RNA polymerase is added and the sample is incubated at 37° C. for approximately 25 minutes for the synthesis of RNA. The above steps are then repeated. Alternatively, after the initial cDNA synthesis, both RT and RNA polymerase are added following a 1 minute 100° C. denaturation followed by an RNA elongation of approximately 30 minutes at 37° C. TAS can be also be performed on solid phase as according to Wylie et al., *J Clin Micro*, 36(12):3488-3491 (1998). In this method, nucleic acid targets are captured with magnetic beads containing specific capture primers. The beads with captured targets are washed and pelleted before adding amplification reagents which contains amplification primers, dNTP, NTP, 2500 U of reverse transcriptase and 2500 U of T7 RNA polymerase. A 100 µl TMA reaction mixture is placed in a tube, 200 µl oil reagent is added and amplification is accomplished by incubation at 42° C. in a waterbath for one hour.

NASBA is a transcription-based amplification method which amplifies RNA from either an RNA or DNA target. NASBA is a method used for the continuous amplification of nucleic acids in a single mixture at one temperature. For example, for RNA amplification, avian myeloblastosis virus (AMV) reverse transcriptase, RNase H and T7 RNA polymerase are used. This method can be performed as according to Heim, et al., *Nucleic Acids Res.*, 26(9):2250-2251 (1998). Briefly, an NASBA reaction mixture contains two specific primers, dNTP, NTP, 6.4 U of AMV reverse transcriptase, 0.08 U of *E. coli* Rnase H, and 32 U of T7 RNA polymerase. The amplification is carried out for 120 min at 41° C. in a total volume of 20 µl.

In a related method, self-sustained sequence-replication (3SR) reaction, isothermal amplification of target DNA or RNA sequences in vitro using three enzymatic activities: reverse transcriptase, DNA-dependent RNA polymerase and *E. coli* ribonuclease H. This method may be modified from a 3-enzyme system to a 2-enzyme system by using human immunodeficiency virus (HIV)-1 reverse transcriptase instead of avian myeloblastosis virus (AMV) reverse transcriptase to allow amplification with T7 RNA polymerase but without *E. coli* ribonuclease H. In the 2-enzyme 3SR, the amplified RNA is obtained in a purer form compared with the 3-enzyme 3SR (Gebinoga & Oehlenschlager *Eur J Biochem*, 235:256-261, 1996).

SDA is an isothermal nucleic acid amplification method. A primer containing a restriction site is annealed to the template. Amplification primers are then annealed to 5' adjacent sequences (forming a nick) and amplification is started at a fixed temperature. Newly synthesized DNA strands are nicked by a restriction enzyme and the polymerase amplification begins again, displacing the newly synthesized strands. SDA can be performed as according to Walker, et al., *PNAS*, 89:392-6 (1992). Briefly, an SDA reaction mixture contains four SDA primers, dGTP, dCTP, TTP, dATP, 150 U of Hinc II, and 5 U of exonuclease-deficient of the large fragment of *E. coli* DNA polymerase I (exo$^-$ Klenow polymerase). The sample mixture is heated 95° C. for 4 minutes to denature target DNA prior to addition of the enzymes. After addition of the two enzymes, amplification is carried out for 120 min. at 37° C. in a total volume of 50 µl. Then, the reaction is terminated by heating for 2 min. at 95° C.

The Q-beta replication system uses RNA as a template. Q-beta replicase synthesizes the single-stranded RNA genome of the coliphage Qβ. Cleaving the RNA and ligating in a nucleic acid of interest allows the replication of that sequence when the RNA is replicated by Q-beta replicase (Kramer & Lizardi *Trends Biotechnol.* 1991 9(2):53-8, 1991).

In suitable embodiments, PCR is used to amplify a target sequence of interest. PCR is a technique for making many copies of a specific template DNA sequence. The reaction consists of multiple amplification cycles and is initiated using a pair of primer sequences that hybridize to the 5' and 3' ends of the sequence to be copied. The amplification cycle includes an initial denaturation, and typically up to 50 cycles of annealing, strand elongation and strand separation (denaturation). In each cycle of the reaction, the DNA sequence between the primers is copied. Primers can bind to the copied DNA as well as the original template sequence, so the total number of copies increases exponentially with time. PCR can be performed as according to Whelan, et al., *J of Clin Micro*, 33(3):556-561(1995). Briefly, a PCR reaction mixture includes two specific primers, dNTPs, approximately 0.25 U of Taq polymerase, and 1×PCR Buffer.

The skilled artisan is capable of designing and preparing primers that are appropriate for amplifying a target or marker sequence. The length of the amplification primers depends on several factors including the nucleotide sequence identity and the temperature at which these nucleic acids are hybridized or used during in vitro nucleic acid amplification. The considerations necessary to determine a preferred length for an amplification primer of a particular sequence identity are well-known to a person of ordinary skill. For example, the length of a short nucleic acid or oligonucleotide can relate to its hybridization specificity or selectivity.

In some embodiments, the amplification may include a labeled primer probe, thereby allowing detection of the amplification products corresponding to that primer or probe. In particular embodiments, the amplification may include a multiplicity of labeled primers or probes; typically, such primers are distinguishably labeled, allowing the simultaneous detection of multiple amplification products.

In one embodiment, a primer or probe is labeled with a fluorogenic reporter dye that emits a detectable signal. While a suitable reporter dye is a fluorescent dye, any reporter dye that can be attached to a detection reagent such as an oligonucleotide probe or primer is suitable for use in the invention. Such dyes include, but are not limited to, Acridine, AMCA, BODIPY, Cascade Blue, Cy2, Cy3, Cy5, Cy7, Edans, Eosin, Erythrosin, Fluorescein, 6-Fam, Tet, Joe, Hex, Oregon Green, Rhodamine, Rhodol Green, Tamra, Rox, and Texas Red.

In yet another embodiment, the detection reagent may be further labeled with a quencher dye such as Tamra, Dabcyl, or Black Hole Quencher® (BHQ), especially when the reagent is used as a self-quenching probe such as a TaqMan® (U.S. Pat. Nos. 5,210,015 and 5,538,848) or Molecular Beacon probe (U.S. Pat. Nos. 5,118,801 and 5,312,728), or other stemless or linear beacon probe (Livak et al., 1995, *PCR Method Appl.*, 4:357-362; Tyagi et al, 1996, *Nature Biotechnology*, 14:303-308; Nazarenko et al., 1997, *Nucl. Acids Res.*, 25:2516-2521; U.S. Pat. Nos. 5,866,336 and 6,117,635).

Nucleic acids may be amplified prior to detection or may be detected directly during an amplification step (i.e., "real-time" methods). In some embodiments, the target sequence is amplified and the resulting amplicon is detected by electrophoresis. In some embodiments, the target sequence is amplified using a labeled primer such that the resulting amplicon is detectably labeled. In some embodiments, the primer is fluorescently labeled.

In one embodiment, detection of a target nucleic acid, such as a nucleic acid from a *lactobacillus* or pathogenic bacteria, is performed using the TaqMan® assay, which is also known as the 5' nuclease assay (U.S. Pat. Nos. 5,210,015 and 5,538,848). The TaqMan® assay detects the accumulation of a specific amplified product during PCR. The TaqMan® assay utilizes an oligonucleotide probe labeled with a fluorescent reporter dye and a quencher dye. The reporter dye is excited by irradiation at an appropriate wavelength, it transfers energy to the quencher dye in the same probe via a process called fluorescence resonance energy transfer (FRET). When attached to the probe, the excited reporter dye does not emit a signal. The proximity of the quencher dye to the reporter dye in the intact probe maintains a reduced fluorescence for the reporter. The reporter dye and quencher dye may be at the 5' most and the 3' most ends, respectively or vice versa. Alternatively, the reporter dye may be at the 5' or 3' most end while the quencher dye is attached to an internal nucleotide, or vice versa. In yet another embodiment, both the reporter and the quencher may be attached to internal nucleotides at a distance from each other such that fluorescence of the reporter is reduced.

During PCR, the 5' nuclease activity of DNA polymerase cleaves the probe, thereby separating the reporter dye and the quencher dye and resulting in increased fluorescence of the reporter. Accumulation of PCR product is detected directly by monitoring the increase in fluorescence of the reporter dye. The DNA polymerase cleaves the probe between the reporter dye and the quencher dye only if the probe hybridizes to the target-containing template which is amplified during PCR.

TaqMan® primer and probe sequences can readily be determined using the variant and associated nucleic acid sequence information provided herein. A number of computer programs, such as Primer Express (Applied Biosystems, Foster City, Calif.), can be used to rapidly obtain optimal primer/probe sets. It will be apparent to one of skill in the art that such primers and probes for detecting the target nucleic acids are useful in diagnostic assays for BV and related pathologies, and can be readily incorporated into a kit format. The present invention also includes modifications of the TaqMan® assay well known in the art such as the use of Molecular Beacon probes (U.S. Pat. Nos. 5,118,801 and 5,312,728) and other variant formats (U.S. Pat. Nos. 5,866, 336 and 6,117,635). Exemplary TaqMan® primers and probes for various target nucleic acids are shown in Tables 1, 2, and 3.

In an illustrative embodiment, real time PCR is performed using TaqMan® probes in combination with a suitable amplification/analyzer such as the ABI Prism® 7900HT Sequence Detection System. The ABI PRISM® 7500 Sequence Detection System is a real-time PCR system that detects and quantitates nucleic acid sequences. Real time detection on the ABI Prism 7500 or 7500 Sequence Detector monitors fluorescence and calculates Rn during each PCR cycle. The threshold cycle, or Ct value, is the cycle at which fluorescence intersects the threshold value. The threshold value is determined by the sequence detection system software or manually. The Ct can be correlated to the initial amount of nucleic acids or number of starting cells using a standard curve.

Other methods of probe hybridization detected in real time can be used for detecting amplification a target or marker sequence flanking a tandem repeat region. For example, the commercially available MGB Eclipse™ probes (Epoch Biosciences), which do not rely on a probe degradation can be used. MGB Eclipse™ probes work by a hybridization-triggered fluorescence mechanism. MGB Eclipse™ probes have the Eclipse™ Dark Quencher and the MGB positioned at the 5'-end of the probe. The fluorophore is located on the 3'-end of the probe. When the probe is in solution and not hybridized, the three dimensional conformation brings the quencher into close proximity of the fluorophore, and the fluorescence is quenched. However, when the probe anneals to a target or marker sequence, the probe is unfolded, the quencher is moved from the fluorophore, and the resultant fluorescence can be detected.

Oligonucleotide probes can be designed which are between about 10 and about 100 nucleotides in length and hybridize to the amplified region. Oligonucleotides probes are preferably 12 to 70 nucleotides; more preferably 15-60 nucleotides in length; and most preferably 15-25 nucleotides in length. The probe may be labeled. Amplified fragments may be detected using standard gel electrophoresis methods. For example, in some embodiments, amplified fractions are separated on an agarose gel and stained with ethidium bromide by methods known in the art to detect amplified fragments.

Internal Control Nucleic Acids

As a quality control measure, an internal amplification control may be included in one or more samples to be extracted and amplified. The skilled artisan will understand that any detectable sequence that is not derived from the target bacterial species can be used as the control sequence. A control sequence can be produced synthetically. If PCR amplification is successful, the internal amplification control amplicons can then be detected. Additionally, if included in the sample prior to purification of nucleic acids, the control sequences can also act as a positive purification control.

Kits

In a further aspect, the invention disclosure provides kits for diagnosing BV in an individual, the kit comprising: a set of reagents for determining the presence or absence, or differential presence, of one or more bacteria indicative of BV. In one embodiment, the kit contains a set of nucleic acid primers for detecting one or more *lactobacilli* and two or more pathogenic organisms in a sample. For example, the kit may comprise a primer pair for amplifying a fragment of a nucleic acid from one or more *lactobacilli* and primer pairs for amplifying fragments of nucleic acids two or more pathogenic organisms. In one embodiment, at least one primer pair is selected from the group consisting of: SEQ ID NOs: 1/2, SEQ ID NOs: 4/5, SEQ ID NOs: 8/9; SEQ ID NOs: 11/12; SEQ ID NOs: 14-15; and SEQ ID NOs: 17/18. In exemplary embodiments, the kit contains one or more of the primers or probes of SEQ ID NOs: 1-19.

EXAMPLE

The present invention is further illustrated by the following examples, which should not be construed as limiting in any way.

In this Example, single and multiplex PCR assays for various bacteria associated with bacterial vaginosis were conducted. The "subassays" in this study used specific target primer/probe sets for amplification and detection of DNA extracts using TaqMan® technology. The primers hybridized to flanking regions within the 16S ribosomal RNA gene of the target species, but did not bind to the same region. The probes used for detection of the amplicon are labeled with a 5' reporter dye and a 3' quencher dye and binds to a sequence of the 16S gene, which is unique to the appropriate species.

Materials and Methods

Vaginal samples from patients were collected using the Aptima swab transport media. Swab transport media is included in the Aptima Vaginal Swab Collection Kit (Gen-Probe, Catalog No. 1162). The samples were subjected to a sample preparation in which the nucleic acids were released and purified from the other components of the sample using MagNAPure™ LC DNA isolation kit III (Roche Diagnostics GmbH, Germany, Cat No. 3 264 785). The sample preparation yielded a specimen containing the nucleic acids in elution buffer.

The primer and probe set for *Lactobacillus acidophilus/crispatus* were designed to detect the closely related acidophilus and crispatus species of the *Lactobacillus* genus. The sets for *Atopobium vaginae, L., jensenii*, and *L. vaginalis* were specific to the given species, and did not detect other members of genus. The sets for *Lactobacillus ssp, Megasphaera, Gardnerella* and *Mobiluncus* were designed to detect all members of the genus. In Assay A, the probes used to detect both the *L. acidophilus/crispatus* and *L. jensenii* species were labeled with the FAM reporter dye. This means that while all three species can be detected by an increase in FAM fluorescence, concentrations of the three species cannot be distinguished. Thus, the peroxide producers detected by the multiplex assay may be referred to in this study as *Lactobacillus acidophilus/crispatus/jensenii*. The primers and probes for each species are shown in Tables 1-3 above.

To ensure the absence of PCR inhibitors in a sample, an internal positive amplification control (IPC) is included with each specimen. The positive control primers and probe are added to create a multiplex reaction with the target and sample primers. The IPC amplicon is detected with a probe labeled with VIC or JOE as the 5' reporter dye. A sample can be interpreted as negative only if the analysis of the internal positive control indicates that DNA amplification has occurred in the reaction tube. The reaction mixtures for the Assays A, C, and D are shown in Tables 4-6 below, respectively.

TABLE 4

| Assay A PCR Mix | | | |
|---|---|---|---|
| | uL per reaction | Unit of Measure 1000 rxns. | Final Concentration Per reaction |
| Sterile Nuclease Free Water | 8.39 | 8.39 mL | |
| Lacto a/c-F (100 uM) | 0.25 | 250 uL | 500 nM |
| Lacto a/c-R (100 uM) | 0.25 | 250 uL | 500 nM |
| Lacto a/c-P Q670/BHQ2 (100 uM) | 0.05 | 50 uL | 100 nM |
| Lacto je-F (100 uM) | 0.25 | 250 uL | 500 nM |
| Lacto je-R (100 uM) | 0.25 | 250 uL | 500 nM |
| Lacto je-P (100 uM) | 0.05 | 50 uL | 100 nM |
| 10x QIPC2 Mix (VIC/NFQ) | 5 | 5.0 mL | 1x |
| 50x QIPC2 DNA | 0.01 | 10 uL | 0.01x |
| Total | 14.5 | 14.5 mL | |

TABLE 5

| Assay C PCR Mix | | | |
|---|---|---|---|
| | uL per reaction | Unit of Measure 1000 rxns. | Final Concentration Per reaction |
| Sterile Nuclease Free Water | 8.39 | 8.39 mL | |
| Av-F (100 uM) | 0.25 | 250 uL | 500 nM |
| Av-R (100 uM) | 0.25 | 250 uL | 500 nM |
| Av-P (100 uM) | 0.05 | 50 uL | 100 nM |
| Mega-F (100 uM) | 0.25 | 250 uL | 500 nM |
| Mega-R (100 uM) | 0.25 | 250 uL | 500 nM |
| Mega-P (100 uM) | 0.05 | 50 uL | 100 nM |
| 10x QIPC2 Mix (VIC/NFQ) | 5 | 5.0 mL | 1x |
| 50x QIPC2 DNA | 0.01 | 10 uL | 0.01x |
| Total | 14.5 | 14.5 mL | |

TABLE 6

| Assay D PCR Mix | | | |
|---|---|---|---|
| | uL per reaction | Unit of Measure 1000 rxns. | Final Concentration Per reaction |
| Sterile Nuclease Free Water | 8.94 | 8.94 mL | |
| Gv-F (100 uM) | 0.25 | 250 uL | 500 nM |
| Gv-R (100 uM) | 0.25 | 250 uL | 500 nM |
| Gv-P (100 uM) | 0.05 | 50 uL | 100 nM |
| 10x QIPC2 Mix (JOE/EDQ) | 5 | 5.0 mL | 1x |
| 50x QIPC2 DNA | 0.01 | 10 uL | 0.01x |
| Total | 14.5 | 14.5 mL | |

Master mixes were assembled by taking 350 μL of each PCR mix prepared as shown in Tables 4-6 above and combining with 604 μL of TaqMan® Universal 2×PCR Master mix and 12 μL AmpliTaq Gold® DNA polymerase. Cycling parameters for the assay were: 50° C. for 2 min, 95° C. for 10 min, 50 cycles of 95.0° C. for 15 sec to 60° C. for 1 min.

The Amplitaq Gold® polymerase used to amplify the target DNA includes a 5' to 3' exonuclease activity which degrades the bound probe and physically separates the reporter from the quencher dyes, resulting in an increased fluorescent signal. Increased fluorescence is plotted against the PCR cycle. The PCR cycle at which the plot line crosses a chosen cutoff is called the Cycle Threshold (Ct). This is the standard unit of measure in TaqMan® based real-time PCR assays. A lower Ct value indicates an earlier exponential phase for a reaction, and is correlated to a higher initial concentration. The Ct values were compared to a standard curve to give quantitative data of cell concentrations in the original sample.

Results

The Bacterial Vaginosis PCR Assay described above was compared to the traditional Nugent Score procedure for the diagnosis of BV. Sixty-nine (69) patient samples were analyzed both by a microscopic determination of Nugent Score, and by the Bacterial Vaginosis PCR Assay. Quantitative results determined from the Bacterial Vaginosis PCR Assay for patient samples is shown in Table 7.

TABLE 7

Organism Detection by Assay (Units are Log (Cells/ml))

| | Assay A | | Assay B | | | | Individual Assays | | | |
|---|---|---|---|---|---|---|---|---|---|---|
| | Lacto | Lacto | Lacto | Lacto | Assay C | | | | Mobil. | Nugent |
| Sample | a/c | je. | ssp. | a/c/je | A. vaginae | Megasphaera | L. vagin. | Gardnerella | ssp. | Score |
| 1 | | | 5.4 | | 3.7 | 6.3 | | 6.4 | | 4 |
| 2 | 7.1 | 6.9 | 7.0 | 7.0 | | | | | 1.2 | 0 |
| 3 | | 6.8 | 6.4 | | | | | | 2.4 | 0 |
| 4 | 6.6 | | 6.5 | 6.5 | | | | | | 0 |
| 5 | | 6.9 | 6.4 | 6.3 | | | | | 2.8 | 0 |
| 6 | | | 4.7 | | | | | | 3.6 | 1 |
| 7 | 5.1 | 3.7 | 5 | 4.9 | | | | | | 1 |
| 8 | 3.0 | 6.8 | 6.1 | 6.1 | | | 7.3 | | 3.6 | 0 |
| 9 | | | | | | | | | 3.7 | 8 |
| 10 | 6.3 | 5.9 | 6.3 | 6.3 | | | 8.0 | 3.3 | 1.2 | 0 |
| 11 | | | 5.7 | | | | 7.3 | 6.4 | | 6 |
| 12 | | 5.7 | 5.7 | 5.2 | | | 3.7 | | | 0 |
| 13 | | 7.8 | 7.0 | 7.1 | | | | 6.4 | | 6 |
| 14 | 5.5 | 6.9 | 6.5 | 6.5 | | | 8.5 | | | 0 |
| 15 | | | 6.1 | | | | | | | 5 |
| 16 | | | 4.2 | | 7.7 | 8.1 | | 7.8 | | 5 |
| 17 | | 7.1 | 6.3 | 6.5 | | | | | | 3 |
| 18 | | | 5.4 | | | | | | 2.7 | 0 |
| 19 | | | 6.2 | | 7.2 | 8.5 | | 7.9 | 4.3 | 8 |
| 20 | | | 5.9 | | | | 6.2 | | | 0 |
| 21 | 6.5 | 6.1 | 6.5 | 6.5 | | | 6.3 | 4.1 | 3.0 | 0 |
| 22 | | | | | | | | | | 4 |
| 23 | | | 3.9 | | | | | | 2.6 | 1 |
| 24 | | 4.1 | 6.2 | | | | | 4.6 | 2.0 | 8 |
| 25 | | | 6.4 | | | | | | | 0 |
| 26 | | | 5.7 | | | | | | 2.8 | 0 |
| 27 | | | 2.0 | | | | | 6.8 | | 5 |
| 28 | | | | | | | | | | 0 |
| 29 | 6.4 | 6.1 | 6.3 | 6.3 | | | | | | 1 |
| 30 | | | 4.4 | | 6.8 | 7.7 | | 7.3 | 6.7 | 8 |
| 31 | 7.1 | 6.6 | 6.9 | 7.0 | | | 8.3 | | 1.1 | 0 |
| 32 | | | 4.4 | | | | | | 4.2 | 1 |
| 33 | | | | | | | | | 2.7 | 4 |
| 34 | | | 6.2 | | 3.3 | 8.4 | 7.7 | 7.4 | | 4 |
| 35 | 6.0 | | 5.8 | 5.8 | | | | 4.9 | 2.7 | 1 |
| 36 | | | 4.7 | | | | | | 3.8 | 1 |
| 37 | 7.1 | 7.3 | 7.0 | 7.0 | | | 5.1 | | | 0 |
| 38 | 6.5 | 7.0 | 6.6 | 6.6 | | | | | | 0 |
| 39 | | | 6.0 | | | | | 5.6 | 3.9 | 0 |
| 40 | | | 5.1 | | | | | | 1.7 | 0 |
| 41 | | | 5.1 | | | | | 4.3 | 3.7 | 0 |
| 42 | | | 5.9 | | | | 5.3 | 4.4 | 1.6 | 3 |
| 43 | | | 4.5 | | | | | | 2.5 | 6 |
| 44 | 6.5 | 6.6 | 6.5 | 6.5 | | | 7.7 | | 3.7 | 1 |
| 45 | 6.3 | 7.9 | 7 | 7.1 | | | | 7.4 | 1.8 | 5 |
| 46 | 6.1 | 6.7 | 6.2 | 6.2 | | | | | | 1 |
| 47 | | | 4.9 | | | | | | | 6 |
| 48 | | | 5.7 | | | | | | | 2 |
| 49 | 5.9 | | 5.8 | 5.7 | | | 5.7 | | 1.3 | 0 |
| 50 | | 7.3 | 6.5 | 6.6 | | | 5.8 | | 1.3 | 0 |
| 51 | | | 5.5 | | 6.1 | 7.8 | | 7.6 | | 8 |
| 52 | | | | | | | | 5.0 | | 4 |
| 53 | | | 5.5 | | | | | | | 0 |
| 54 | | | 2.3 | | 4.8 | | | 6.3 | | 6 |
| 55 | | | | | | | | 2.2 | | 6 |
| 56 | | 6.6 | 6.1 | 6.0 | | | | | | 0 |
| 57 | | | 5.1 | | | | 4.3 | 6.2 | 5.5 | 1 |
| 58 | 6.4 | | 6.2 | 6.3 | | | | | 2.4 | 0 |
| 59 | 5.8 | 6.3 | 5.9 | 6.0 | | | | | | 0 |
| 60 | | | 4.7 | | | | | | 2.7 | 1 |
| 61 | 4.9 | | 4.9 | 4.7 | | | | 4.2 | | 8 |
| 62 | 3.4 | | 5.1 | 0.5 | 4.5 | | 8.2 | 6.4 | 3.6 | 0 |
| 63 | | 6.7 | 6.0 | 6.0 | | | | | | 0 |
| 64 | | | 5.3 | | | | | | | 0 |
| 65 | 6.3 | | 6.2 | 6.2 | | | 7.0 | | | 0 |
| 66 | | | 4.7 | | | | | | 2.2 | 4 |

TABLE 7-continued

Organism Detection by Assay (Units are Log (Cells/ml))

| | Assay A | | Assay B | | | | Individual Assays | | | |
|---|---|---|---|---|---|---|---|---|---|---|
| Sample | Lacto a/c | Lacto je. | Lacto ssp. | Lacto a/c/je | A. vaginae | Megasphaera | L. vagin. | Gardnerella | Mobil. ssp. | Nugent Score |
| 67 | 6.3 | 5.5 | 6.2 | 6.1 | | | 9.1 | 6.6 | | 0 |
| 68 | | 6.8 | 6.1 | 6.1 | | | | | 3.0 | 0 |
| 69 | 6.2 | | 6.0 | 6.0 | | | | | | 0 |

The samples presented in Table 7 were categorized based on Nugent Score. FIG. 1 shows the percent of swab specimens containing bacterial agents as arranged by Nugent Score. For some organisms, in particular *Lactobacillus* ssp. and *Mobiluncus*, the percent of specimens containing these organisms do not differ dramatically given disease state. However, dramatic differences exist for the peroxide-producing *lactobacilli* (*Lactobacillus acidophilus/crispatus*, *L. jensenii*, and *L. vaginalis*). Dramatic increases also exist for *A. vaginae*, *Megasphaera* ssp., and *Gardnerella*. In this study, *Atopobium* and *Megasphaera* both appear in 57% of samples given a diagnosis of BV based on Nugent score. *Gardnerella* appears in 85% of BV samples.

Figure 2:
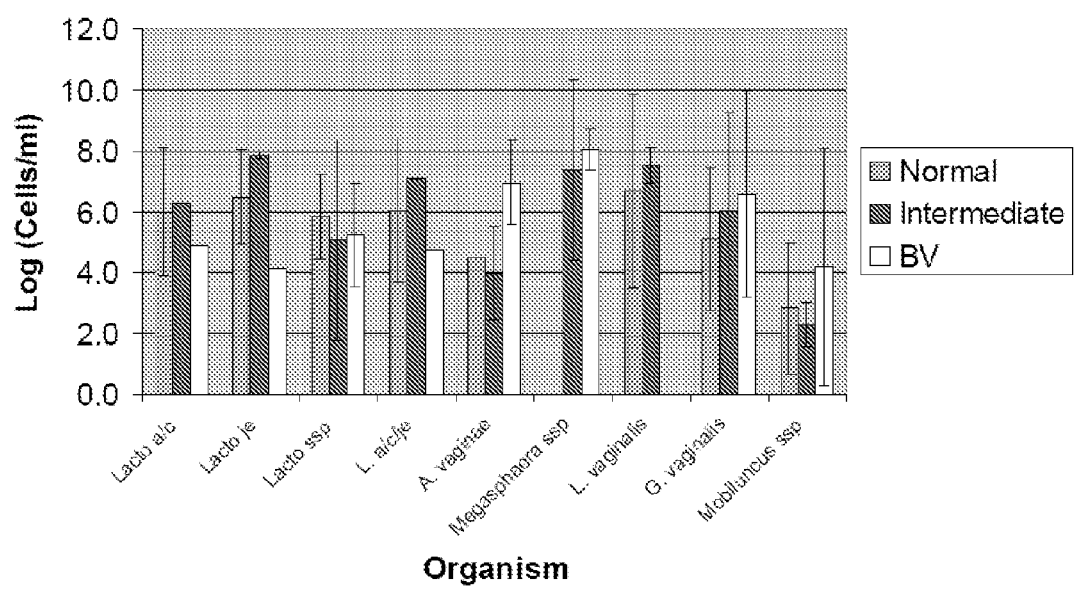
FIG. 2 is a chart showing the mean quantities of bacterial agents in swab specimens from patients arranged by Nugent Score. The bacterial agents were detected according to an illustrative embodiment of the invention.

FIG. 2 shows the mean quantities of bacterial agents as arranged by Nugent Score. Samples in which none of a given agent was detected were not included in statistics. Error bars show ±2 standard deviations. For most organisms, a broad overlap exists between cell counts for the different disease states. More dramatic differences in mean exist between disease states for *Atopobium*, *Megasphaera*, *Gardnerella*, *L. acidophilus/crispatus*, *L. jensenii*, and *L. vaginalis*.

Analysis of BV PCR Test Results Using Algorithms

Algorithms 1-8 (described above) were used to create a ratio based on the quantity of various organisms in a vaginal swab sample from a patient. Table 8 shows the ratios produced by each algorithm. Algorithms 1-4 were derived by adding the Logs of the quantities for each target organism (Sum of Logs). Algorithms 5-8 were derived by adding the quantities first, and then taking the Log of the result (Log of Sums).

TABLE 8

Analysis of BV PCR Test Results Using Algorithms

| | | | Algorithm | | | | | | | |
|---|---|---|---|---|---|---|---|---|---|---|
| | Nugent | Semi | Sum of Logs | | | | Log of Sums | | | |
| Sample | Score | Quant | 1 | 2 | 3 | 4 | 5 | 6 | 7 | 8 |
| 1 | 4 | BV | 0.53 | 0.10 | 0.06 | 0.06 | 0.85 | 0.16 | 0.15 | 0.15 |
| 2 | 0 | Norm | 14.05 | 13.91 | 13.91 | 13.91 | 7.32 | 7.27 | 7.27 | 7.27 |
| 3 | 0 | Norm | 12.83 | 6.85 | 6.85 | 6.85 | 6.72 | 6.85 | 6.85 | 6.85 |
| 4 | 0 | Norm | 13.00 | 6.56 | 6.56 | 6.56 | 6.8 | 6.56 | 6.56 | 6.56 |
| 5 | 0 | Norm | 12.70 | 6.89 | 6.89 | 6.89 | 6.66 | 6.89 | 6.89 | 6.89 |
| 6 | 1 | Int | 4.69 | 1.00 | 1.00 | 1.00 | 4.69 | 1.00 | 1.00 | 1.00 |
| 7 | 1 | Norm | 9.85 | 8.8 | 8.8 | 8.8 | 5.23 | 5.08 | 5.08 | 5.08 |
| 8 | 0 | Norm | 12.21 | 9.75 | 9.75 | 17.05 | 6.41 | 6.77 | 6.77 | 7.41 |
| 9 | 8 | Norm | 1.00 | 1.00 | 1.00 | 1.00 | 1.00 | 1.00 | 1.00 | 1.00 |
| 10 | 0 | Norm | 12.6 | 12.2 | 3.68 | 6.08 | 6.6 | 6.44 | 1.94 | 2.41 |
| 11 | 6 | BV | 5.66 | 1.00 | 0.16 | 1.14 | 5.66 | 1.00 | 0.16 | 1.14 |
| 12 | 0 | Norm | 10.94 | 5.71 | 5.71 | 9.46 | 5.85 | 5.71 | 5.71 | 5.71 |
| 13 | 6 | Int | 14.04 | 7.80 | 1.22 | 1.22 | 7.33 | 7.80 | 1.22 | 1.22 |
| 14 | 0 | Norm | 12.95 | 12.41 | 12.41 | 20.88 | 6.77 | 6.95 | 6.95 | 8.48 |
| 15 | 5 | Norm | 6.10 | 1.00 | 1.00 | 1.00 | 6.10 | 1.00 | 1.00 | 1.00 |
| 16 | 5 | BV | 0.27 | 0.06 | 0.04 | 0.04 | 0.51 | 0.12 | 0.12 | 0.12 |
| 17 | 3 | Norm | 12.07 | 7.12 | 7.12 | 7.12 | 6.70 | 7.12 | 7.12 | 7.12 |
| 18 | 0 | Norm | 5.42 | 1.00 | 1.00 | 1.00 | 5.42 | 1.00 | 1.00 | 1.00 |
| 19 | 8 | BV | 0.39 | 0.06 | 0.04 | 0.04 | 0.73 | 0.12 | 0.12 | 0.12 |
| 20 | 0 | Norm | 5.89 | 1.00 | 1.00 | 6.17 | 5.89 | 1.00 | 1.00 | 1.00 |
| 21 | 0 | Norm | 13.07 | 12.57 | 3.09 | 4.65 | 6.83 | 6.62 | 1.63 | 1.67 |
| 22 | 4 | Norm | 1.00 | 1.00 | 1.00 | 1.00 | 1.00 | 1.00 | 1.00 | 1.00 |
| 23 | 1 | Norm | 3.93 | 1.00 | 1.00 | 1.00 | 3.93 | 1.00 | 1.00 | 1.00 |
| 24 | 8 | Norm | 6.16 | 4.12 | 0.91 | 0.91 | 0.16 | 4.12 | 0.91 | 0.91 |
| 25 | 0 | Norm | 6.45 | 1.00 | 1.00 | 1.00 | 6.45 | 1.00 | 1.00 | 1.00 |
| 26 | 0 | Norm | 5.69 | 1.00 | 1.00 | 1.00 | 5.69 | 1.00 | 1.00 | 1.00 |
| 27 | 5 | BV | 2.04 | 1.00 | 0.15 | 0.15 | 2.04 | 1.00 | 0.15 | 0.15 |
| 28 | 0 | Norm | 1.00 | 1.00 | 1.00 | 1.00 | 1.00 | 1.00 | 1.00 | 1.00 |
| 29 | 1 | Norm | 12.51 | 12.46 | 12.46 | 12.46 | 6.56 | 6.55 | 6.55 | 6.55 |
| 30 | 8 | BV | 0.31 | 0.07 | 0.05 | 0.05 | 0.57 | 0.13 | 0.13 | 0.13 |
| 31 | 0 | Norm | 13.90 | 13.70 | 13.70 | 22.03 | 7.25 | 7.20 | 7.20 | 8.36 |
| 32 | 1 | Norm | 4.41 | 1.00 | 1.00 | 1.00 | 4.41 | 1.00 | 1.00 | 1.00 |
| 33 | 4 | Norm | 1.00 | 1.00 | 1.00 | 1.00 | 1.00 | 1.00 | 1.00 | 1.00 |
| 34 | 4 | BV | 0.53 | 0.09 | 0.05 | 0.40 | 0.74 | 0.12 | 0.12 | 0.91 |
| 35 | 1 | Norm | 11.67 | 6.02 | 1.24 | 1.24 | 6.14 | 6.02 | 1.24 | 1.24 |
| 36 | 1 | Norm | 4.71 | 1.00 | 1.00 | 1.00 | 4.71 | 1.00 | 1.00 | 1.00 |

TABLE 8-continued

Analysis of BV PCR Test Results Using Algorithms

| | | | Algorithm | | | | | | | |
|---|---|---|---|---|---|---|---|---|---|---|
| | Nugent | Semi | Sum of Logs | | | | Log of Sums | | | |
| Sample | Score | Quant | 1 | 2 | 3 | 4 | 5 | 6 | 7 | 8 |
| 37 | 0 | Norm | 14.02 | 14.36 | 14.36 | 19.46 | 7.31 | 7.49 | 7.49 | 7.49 |
| 38 | 0 | Norm | 13.23 | 13.56 | 13.56 | 13.56 | 6.92 | 7.16 | 7.16 | 7.16 |
| 39 | 0 | Int | 6.02 | 1.00 | 0.18 | 0.18 | 6.02 | 1.00 | 0.18 | 0.18 |
| 40 | 0 | Norm | 5.14 | 1.00 | 1.00 | 1.00 | 5.14 | 1.00 | 1.00 | 1.00 |
| 41 | 0 | Norm | 5.08 | 1.00 | 0.23 | 0.23 | 5.08 | 1.00 | 0.23 | 0.23 |
| 42 | 3 | Norm | 5.89 | 1.00 | 0.23 | 1.19 | 5.89 | 1.00 | 0.23 | 1.19 |
| 43 | 6 | Norm | 4.52 | 1.00 | 1.00 | 1.00 | 4.52 | 1.00 | 1.00 | 1.00 |
| 44 | 1 | Norm | 12.97 | 13.15 | 13.15 | 20.84 | 6.79 | 6.88 | 6.88 | 7.76 |
| 45 | 5 | Int | 14.08 | 14.19 | 1.92 | 1.92 | 7.34 | 7.90 | 1.07 | 1.07 |
| 46 | 1 | Norm | 12.43 | 12.77 | 12.77 | 12.77 | 6.52 | 6.78 | 6.78 | 6.78 |
| 47 | 6 | Norm | 4.87 | 1.00 | 1.00 | 1.00 | 4.87 | 1.00 | 1.00 | 1.00 |
| 48 | 2 | Norm | 5.70 | 1.00 | 1.00 | 1.00 | 5.70 | 1.00 | 1.00 | 1.00 |
| 49 | 0 | Norm | 11.52 | 5.88 | 5.88 | 11.60 | 6.07 | 5.88 | 5.88 | 6.11 |
| 50 | 0 | Norm | 13.13 | 7.31 | 7.31 | 13.10 | 6.87 | 7.31 | 7.31 | 7.32 |
| 51 | 8 | BV | 0.40 | 0.07 | 0.05 | 0.05 | 0.70 | 0.12 | 0.12 | 0.12 |
| 52 | 4 | Int | 1.00 | 1.00 | 0.20 | 0.20 | 1.00 | 1.00 | 0.20 | 0.20 |
| 53 | 0 | Norm | 5.48 | 1.00 | 1.00 | 1.00 | 5.48 | 1.00 | 1.00 | 1.00 |
| 54 | 6 | BV | 0.48 | 0.21 | 0.09 | 0.09 | 0.48 | 0.21 | 0.16 | 0.16 |
| 55 | 6 | Norm | 1.00 | 1.00 | 0.46 | 0.46 | 1.00 | 1.00 | 0.46 | 0.46 |
| 56 | 0 | Norm | 12.01 | 6.61 | 6.61 | 6.61 | 6.31 | 6.61 | 6.61 | 6.61 |
| 57 | 1 | BV | 5.13 | 1.00 | 0.16 | 0.70 | 5.13 | 1.00 | 0.16 | 0.70 |
| 58 | 0 | Norm | 12.54 | 6.39 | 6.39 | 6.39 | 6.57 | 6.30 | 6.39 | 6.39 |
| 59 | 0 | Norm | 11.90 | 12.07 | 12.07 | 12.07 | 6.26 | 6.39 | 6.39 | 6.39 |
| 60 | 1 | Norm | 4.73 | 1.70 | 1.70 | 1.70 | 4.73 | 1.70 | 1.70 | 1.70 |
| 61 | 8 | Int | 9.6 | 4.88 | 1.15 | 1.15 | 5.11 | 4.88 | 1.15 | 1.15 |
| 62 | 0 | Int | 1.24 | 0.75 | 0.31 | 1.06 | 1.13 | 0.75 | 0.53 | 1.27 |
| 63 | 0 | Norm | 12.01 | 6.67 | 6.67 | 6.67 | 6.3 | 6.67 | 6.67 | 6.67 |
| 64 | 0 | Norm | 5.29 | 1.00 | 1.00 | 1.00 | 5.29 | 1.00 | 1.00 | 1.00 |
| 65 | 0 | Norm | 12.42 | 6.32 | 6.32 | 13.35 | 6.51 | 6.32 | 6.32 | 7.10 |
| 66 | 4 | Norm | 4.74 | 1.00 | 1.00 | 1.00 | 4.74 | 1.00 | 1.00 | 1.00 |
| 67 | 0 | Int | 12.25 | 11.78 | 1.78 | 3.17 | 6.43 | 6.34 | 0.95 | 1.38 |
| 68 | 0 | Norm | 12.20 | 6.79 | 6.79 | 6.79 | 6.40 | 6.79 | 6.79 | 6.79 |
| 69 | 0 | Norm | 12.03 | 6.19 | 6.19 | 6.19 | 6.32 | 6.19 | 6.19 | 6.19 |

Table 9 shows the division of samples into the three disease classes by both the Nugent Score and the score determined from the Bacterial Vaginosis PCR test using Algorithm 6, which includes data from Assay A (*L. acidophilus/crispatus* and *L. jensenii*) and Assay C (*Atopobium vaginae* and *Megasphaera* ssp.). Ratio results from 0 to 0.199 were given a diagnosis of BV, 0.2 to 4.99 a diagnosis of intermediate, and 5 and above a diagnosis of normal.

TABLE 9

Concordance between Nugent Score Results and Results from Bacterial Vaginosis Assay by PCR.

| | | Diagnosis Using PCR Assay for BV (Algorithm 6) | | | |
|---|---|---|---|---|---|
| | | BV | Intermediate | Normal | |
| Nugent | BV | 4 | 3 | 0 | 7 |
| Score | Intermediate | 2 | 11 | 2 | 15 |
| | Normal | 0 | 19 | 28 | 47 |
| | | 6 | 33 | 30 | |

Sensitivity: 57%
Specificity: 60%
Concordance: 62%

The sensitivity refers to the detection of BV by the PCR assay of samples that were also positive for BV by the Nugent Score. The specificity refers to the determination of normal samples by PCR that were also normal by a Nugent Score. Total concordance (agreement for all three classes divided by the total samples) was 62%.

Table 10 also includes data for *Gardnerella* in the diagnostic score. The results for this table were derived using Algorithm 7 which includes data from Assay A, Assay C and Assay D. Ratio results from 0 to 0.199 were given a diagnosis of BV, 0.2 to 4.99 a diagnosis of intermediate, and 5 and above a diagnosis of normal.

TABLE 10

Concordance between Nugent Score Results and Results from Bacterial Vaginosis Assay by PCR including *Gardnerella* data.

| | | Diagnosis Using PCR Assay for BV (Algorithm 7) | | | |
|---|---|---|---|---|---|
| | | BV | Intermediate | Normal | |
| Nugent | BV | 4 | 3 | 0 | 7 |
| Score | Intermediate | 5 | 10 | 0 | 15 |
| | Normal | 1 | 22 | 24 | 47 |
| | | 10 | 35 | 24 | |

Sensitivity: 57%
Specificity: 51%
Concordance: 55%

Table 11 includes data for both *Gardnerella* and *L. vaginalis*. The determination of a diagnostic score used Algorithm 8. Ratio results from 0 to 0.199 were given a diagnosis of BV, 0.2 to 4.99 a diagnosis of intermediate, and 5 and above a diagnosis of normal.

TABLE 11

Concordance between Nugent Score Results and Results from Bacterial Vaginosis Assay by PCR including *Gardnerella* and *L. vaginalis* data.

|  |  | Diagnosis Using PCR Assay for BV (Algorithm 8) | | | |
|---|---|---|---|---|---|
|  |  | BV | Intermediate | Normal | |
| Nugent Score | BV | 4 | 3 | 0 | 7 |
|  | Intermediate | 3 | 12 | 0 | 15 |
|  | Normal | 0 | 22 | 25 | 47 |
|  |  | 7 | 37 | 25 | |

Sensitivity: 57%
Specificity: 53%
Concordance: 59%

The sensitivity refers to the detection of BV by the PCR assay of samples that were also positive for BV by the Nugent Score. The specificity refers to the determination of normal samples by PCR that were also normal by a Nugent Score. Concordance using *Gardnerella* with or without *L. vaginalis* was 55% and 59%, respectively.

Table 12 shows concordance between Nugent Score results and results from Bacterial Vaginosis by PCR using a semi-quantitative algorithm. The semi-quantitative algorithm considers the presence or absence of key organisms. A sample is considered normal (not indicative of BV) if: (1) *L. acidophilus*, *L. crispatus*, or *L. jensenii* are present, *Atopobium* and *Megasphaera* are absent, and *Gardnerella* is present in amounts less than $10^6$ cells/ml; or (2) all organisms are absent. A sample is intermediate if: (1) the sample contains both *lactobacilli* and at least one pathogen (>$10^6$ cells/ml for *Gardnerella*); or (2) all organisms are absent except for *Gardnerella*, which is present, but is less than $10^6$ cells/ml, see Table 13. The concordance using the semi-quantitative algorithm was 71%.

TABLE 12

Concordance between Nugent Score Results and Results from Bacterial Vaginosis Assay by PCR Using a Semi-Quantitative Algorithm.

|  |  | Diagnosis Using PCR Assay for BV (Semi-Quantitative Algorithm) | | | |
|---|---|---|---|---|---|
|  |  | BV | Intermediate | Normal | |
| Nugent Score | BV | 4 | 1 | 2 | 7 |
|  | Intermediate | 5 | 3 | 7 | 15 |
|  | Normal | 1 | 4 | 42 | 47 |
|  |  | 10 | 8 | 51 | |

Sensitivity: 57%
Specificity: 89%
Concordance: 71%

TABLE 13

Classification of Subjects based on Detection of Various Bacteria.

|  | Normal | | Intermediate | | BV |
|---|---|---|---|---|---|
| *L. acidophilus*/*crispatus* or *L. jensenii* | + | − | + | − | − |
| *Atopobium* or *Megasphaera* | − | − | + | − | + |
| or *Gardnerella* | <6.0 | − | ≥6.0 | <6.0 | ≥6.0 |

Analysis of Method Comparison Data

Significant differences between disease states as determined by Nugent Score were seen in percent positivity for all organisms except for *Lactobacillus* ssp. and *Mobiluncus* ssp. (FIG. 1). For average cell counts, differences between cell counts for samples with different Nugent Scores were most dramatic for *Atopobium*, *Megasphaera*, *L. acidophilus*/*crispatus*, *L. jensenii*, and *L. vaginalis* (FIG. 2). The differences more modest for *Gardnerella* and *Mobiluncus* (FIG. 2).

Similar disease state diagnoses were obtained with both the Sum of Logs and Log of Sums methods of calculating ratios. While these measures can theoretically produce differing disease state calls, they do not do so in this study. The semi-quantitative algorithm may also be used to determine a diagnosis.

These results demonstrate that the BV Real-Time PCR Assay provides at least two distinct advantages over the Nugent Score as a method of diagnosis. First, the assay is able to distinguish peroxide producing *lactobacilli* from other species, which the Nugent Score method does not do. Second, these results support a role for *Atopobium* and *Megasphaera* in BV, which are not detected in the Nugent Score analysis. The detection of these agents by the current assay will aid in diagnosis and contribute further information to the ongoing discussion of agents which cause BV.

Unless otherwise defined, all technical and scientific terms used herein have the same meaning as commonly understood by one of ordinary skill in the art to which this invention belongs. All nucleotide sequences provided herein are presented in the 5' to 3' direction.

The inventions illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

Other embodiments are set forth within the following claims.

What is claimed is:

1. A method for identifying bacterial vaginosis in a human female subject, the method comprising:
   (a) obtaining a vaginal swab sample from the subject;
   (b) measuring levels of *Atopobium vaginae*, *Megasphaera* genus and one or more *Lactobacilli* species selected from the group consisting of *Lactobacillus acidophilus*, *Lactobacillus crispatus*, and *Lactobacillus jensenii* in the sample, wherein the levels of *Atopobium vaginae*, *Megasphaera* genus and of one or more *Lactobacilli* species are detected with one or more oligonucleotides capable of specifically hybridizing to a target nucleic acid sequence from *Atopobium vaginae*, *Megasphaera* genus, *Lactobacillus acidophilus*, *Lactobacillus crispatus*, and/or *Lactobacillus jensenii*, wherein levels of *Gardnerella vaginalis* and *Mobiluncus* sp are not measured; wherein the levels are determined with one or more oligonucleotide primers selected from SEQ ID NOs: 1, 2, 4, 5, 11, 12, 14 and 15, and complements thereof;
   (c) calculating a diagnostic score as the ratio of a logarithmic function of the levels of the one or more *Lactobacilli* species and a logarithmic function of the levels of the *Atopobium vaginae* and *Megasphaera* genus; and
   (d) identifying the subject as having bacterial vaginosis with the diagnostic score lower than a reference score.

2. A method for identifying bacterial vaginosis in a human female subject, the method comprising:
   (a) obtaining a vaginal swab sample from the subject;
   (b) measuring levels of *Atopobium vaginae*, *Megasphaera* genus and one or more *Lactobacilli* species selected from the group consisting of *Lactobacillus acidophilus*, *Lactobacillus crispatus*, and *Lactobacillus jensenii* in the sample, wherein the levels of *Atopobium vaginae*, *Megasphaera* genus and of one or more *Lactobacilli* species are detected with one or more oligonucleotides capable of specifically hybridizing to a target nucleic acid sequence from *Atopobium vaginae*, *Megasphaera* genus, *Lactobacillus acidophilus*, *Lactobacillus crispalus*, and/or *Lactobacillus jensenii*, wherein levels of *Gardnerella vaginalis* and *Mobiluncus* sp are not measured; wherein the levels are determined by PCR with oligonucleotide primer pairs comprising SEQ ID NOs: 1, 2, 4, 5, 11, 12, 14 and 15;

(c) calculating a diagnostic score as the ratio of a logarithmic function of the levels of the one or more *Lactobacilli* species and a logarithmic function of the levels of the *Atopobium vaginae* and *Megasphaera* genus; and
(d) identifying the subject as having bacterial vaginosis with the diagnostic score lower than a reference score.

* * * * *